US008110183B2

United States Patent
Hu et al.

(10) Patent No.: US 8,110,183 B2
(45) Date of Patent: Feb. 7, 2012

(54) METHOD FOR SUSTAINED EXPRESSION OF AN EXOGENOUS GENE

(75) Inventors: Yu-Chen Hu, Hsinchu (TW); Wen-Hsin Lo, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 12/332,838

(22) Filed: Dec. 11, 2008

(65) Prior Publication Data

US 2010/0028880 A1 Feb. 4, 2010

(30) Foreign Application Priority Data

Aug. 4, 2008 (TW) .............................. 97129578 A (51) Int. Cl.
*A01N 63/00* (2006.01)
*C12N 5/00* (2006.01)

(52) U.S. Cl. ...................................... 424/93.2; 435/325

(58) Field of Classification Search ................. 424/93.2; 435/325
See application file for complete search history.

(56) References Cited

U.S. PATENT DOCUMENTS

| 5,348,886 | A | * | 9/1994 | Lee et al. | ..................... 435/69.1 |
| 6,020,169 | A | * | 2/2000 | Lee et al. | ..................... 435/70.1 |
| 6,406,700 | B1 | * | 6/2002 | Srivastava | .................. 424/193.1 |
| 7,393,677 | B2 | * | 7/2008 | Airenne et al. | ............. 435/235.1 |
| 7,527,967 | B2 | * | 5/2009 | Chao et al. | ................. 435/320.1 |

OTHER PUBLICATIONS

Peakman (Nucleic Acids Res., 1992, vol. 20, p. 495-500).*
Miller (1995, FASEB J., vol. 9, p. 190-199).*
Deonarain (1998, Expert Opin. Ther. Pat., vol. 8, p. 53-69).*
Verma (Sep. 1997, Nature, vol. 389, p. 239-242).*
Crystal (1995, Science, vol. 270, p. 404-410).*
Yu-Chen Hu, Current Gene Therapy, Feb. 2008, vol. 8 No. 1: 54-65, Baculoviral Vectros for Gene Delivery: A Review, pp. 1-12.
Wen-HSin Lo et al, The American Society of Gene Therapy, vol. 17, No. 4, Apr. 2009, pp. 658-666.
Shan et al., "An OriP/EBNA-1-based baculovirus vector with prolonged and enchanced transgene expression," J Gene. Med., Dec. 2006, 1400-1406, vol. 8, No. 12.

* cited by examiner

*Primary Examiner* — Michael C. Wilson
(74) *Attorney, Agent, or Firm* — Muncy, Geissler, Olds & Lowe, PLLC (57) ABSTRACT

A method for sustained expression of an exogenous gene forms a circular episomal plasmid to solve the problem of transient expression of baculovirus in the transduced mammalian cells caused by the dilution and degradation when mammalian cells replicate and also prevents dysfunctional cell metabolism.

22 Claims, 9 Drawing Sheets

METHOD FOR SUSTAINED EXPRESSION OF AN EXOGENOUS GENE

BACKGROUND OF THE INVENTION

1. Field of the Invention

The present invention relates to a method for sustained expression of an exogenous gene, and more particularly in sustained expression of an exogenous gene by using baculovirus.

2. Description of the Prior Art

Gene delivery vectors for mammalian cells are classified into non-viral vectors and viral vectors. Non-viral methods of introducing an exogenous gene include various chemical agents and physical methods, e.g. polymer or liposome-mediated transfection or electroporation. However, these methods have following disadvantages including (1) low transfection efficiency for various cell types, especially the primary cells; (2) requirement for a large amount of purified exogenous gene; (3) damage to the cell membranes and disturbance of the cellular physiology.

Viruses possess a number of advantages as an exogenous gene delivery vector, that own high infection efficiency in a wide variety of cell types and tissues, and are provided with an ability of target specificity and enhanced expression of the exogenous gene in vitro and in vivo. Current viral vectors including retroviruses, lentivirus, adenoviruses, adeno-associated viruses and herpesvirus have been employed for gene therapy.

Although the above-mentioned vectors had certain degrees of success in particular application, there are still a variety of obstacles that cannot be surmounted. Plasmid delivery is considered less efficient than viral vectors. Retroviruses integrate viral genes into host cell chromosome resulting in the insertional mutagenesis in host cells or other dysfunction. The French team (2002) found that 9 X linked-SCID patients are cured by using retroviruses as gene delivery vector, but 2 patients were found with leukemia; therefore, there are some safety concerns in adopting retroviruses as gene delivery vectors.

As for adenoviruses, adenoviruses do not integrate viral genes into the host cells but may have safety issues concerning the elicitation of immune responses; in addition, there was a death report in a gene therapy experiment employing adenovirus (1999). Recently, a gutless vector has been developed for mitigating immune responses; however, it needs a helper virus for co-infection in the process of gutless vector production, resulting in more complexity of purifying viral particles. Though adeno-associated viruses (AAV) is safer and enables longer gene expression time, adeno-associated viruses can not deliver large genes because of their own 3.5-4 kb cloning capacity limit, and AAV production can not easily be scaled up due to complicated preparation procedure. Furthermore, adeno-associated viruses are found to integrate viral genes into the host cell chromosome and induce hepatoma in neonatal mice at high viral dosage. Due to these drawbacks, the lack of an ideal vector has been impeding successful application of gene therapy.

On the other hand, baculovirus (*Autographa californica* multiple nucleopolyhedrovirus) is a DNA virus that infects insects as the natural hosts, and has been widely employed for recombinant protein production. However, baculovirus is found to transduce various mammalian cells efficiently, e.g. BHK, CHO, CV-1, HeLa, 293, Cos7, neural cells, human fibroblasts and pancreatic cells, and can drive the expression of exogenous gene under promoters that are active in mammalian cells, e.g. SV-40 (Simian Virus 40) or CMV-IE (cytomegalovirus immediate-early) promoter, without any visible cytopathic effect (CPE). (1995). Besides, it is recently found that baculovirus can transduce bone marrow mesenchymal stem cells with transduction efficiency up to 87%.

Baculovirus vector has following advantages: (1) baculovirus does not replicate and induce cellular toxicity after transducing mammalian cells. Its DNA does not integrate into the host chromosome and is degraded with time; (2) there are no pre-existing antibodies against baculovirus in mammals since the natural hosts of baculovirus are insect cells; (3) baculovirus genome (~130 kb) is much larger than other viral vectors and therefore is able to carry larger and more exogenous genes (at least 38 kb) into cells; (4) baculovirus production can be scaled up by infecting the natural hosts (insect cells) in simple operating procedures; and (5) baculovirus are classified into insect virus and can be operated in bio-safety 1 laboratories. Features (1) to (3) make baculovirus an effective and safer gene delivery vector, features (4) and (5) make baculovirus scaled up in a safe and easy way. These features altogether make baculovirus a good gene therapy vector in mammalian cells. Thanks to these features, baculovirus has hence been developed as a candidate for exogenous gene vector, but a number of roadblocks need to be lifted. One major hurdle is transient expression nature (<7 days) due to its inability to replicate in mammalian cells and has a large genome with multiple recognition sites for many restriction endonucleases. Since the genome of baculovirus cannot replicate in mammalian cells, it is usually degraded or diluted soon after transduction, leading to loss of transgene expression over time.

In general, there are two ways for sustained expression and replication of an exogenous gene in cells. First, the exogenous gene is integrated into host chromosome for the exogenous gene to be replicated with the cellular chromosome. As mentioned above, this method might easily interfere with the normal gene function of cells.

The other method for sustained expression and replication of an exogenous gene is to form a replicable episomal plasmid, wherein the episomal plasmid carries the exogenous gene and includes an origin of replication sequence that is able to allow the episomal plasmid to self-replicate and stably express the exogenous gene in mammalian cells. The episomal plasmid prevents dysfunctional cell metabolism without integrating into the cellular chromosome.

To sum up, the primary goal of this invention to develop a baculovirus vector that allows for the formation of a replicable episomal plasmid for sustained expression of exogenous genes in mammalian cells.

SUMMARY OF THE INVENTION

The present invention is directed to provide a method for sustained expression of an exogenous gene, which forms a circular episomal plasmid to solve the problem of transient expression of baculovirus in the transduced mammalian cell caused by the dilution and degradation when mammalian cells replicate and also to prevent dysfunctional cell metabolism.

According to an embodiment, a method for sustained expression of an exogenous gene includes providing a first recombinant baculovirus comprising a first expression cassette including a recombinase gene; providing a second recombinant baculovirus comprising a second expression cassette including two recombinase recognition sites and an exogenous gene cassette flanked by the recombinase recognition sites, wherein the exogenous gene cassette comprises an origin of replication sequence; and co-transducing with the first recombinant baculovirus and the second recombinant baculovirus into a mammalian cell, whereby the first expression cassette and the second expression cassette are introduced into the mammalian cell, wherein a recombinase expressed by the recombinase gene recognizes and cuts the recombinase recognition sites of the second expression cassette; the second expression cassette is cleaved off from the genome of the second recombinant baculovirus; and the cut recombinase recognition sites of the separated second gene cassette comprising the exogenous expression cassette are self-ligated to form a circular episomal plasmid consisted of one recombinase recognition site and the exogenous gene cassette for sustained expression of the exogenous gene cassette.

Other advantages of the present invention will become apparent from the following description taken in conjunction with the accompanying drawings wherein are set forth, by way of illustration and example, certain embodiments of the present invention.

BRIEF DESCRIPTION OF THE DRAWINGS

The foregoing aspects and many of the accompanying advantages of this invention will become more readily appreciated as the same becomes better understood by reference to the following detailed description, when taken in conjunction with the accompanying drawings, wherein:

FIG. 4a to FIG. 6b are diagrams schematically illustrating the experimental outcomes of an embodiment of the present invention.

DESCRIPTION OF THE PREFERRED EMBODIMENT

Figure 1:
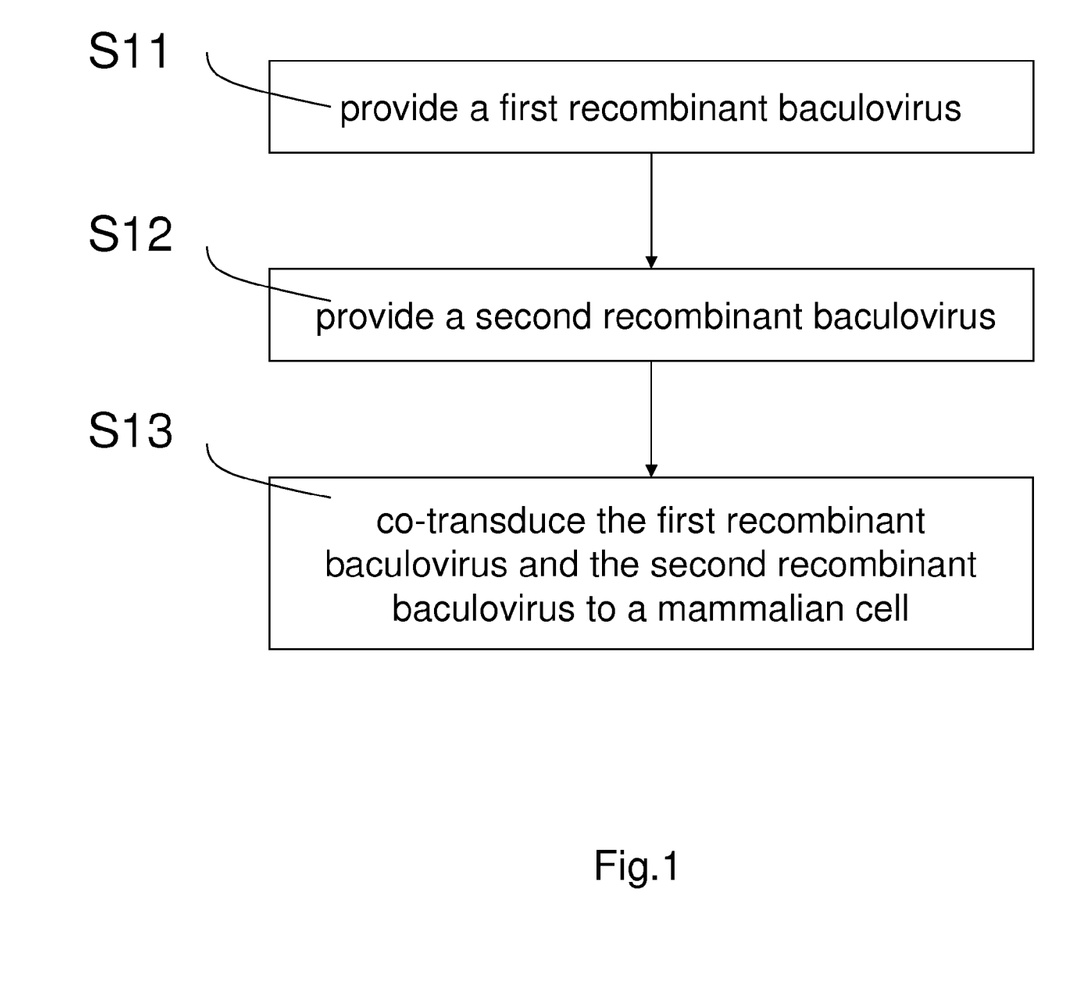
FIG. 1 is a flow chart schematically illustrating a preferred embodiment of the present invention.
Figure 2A:
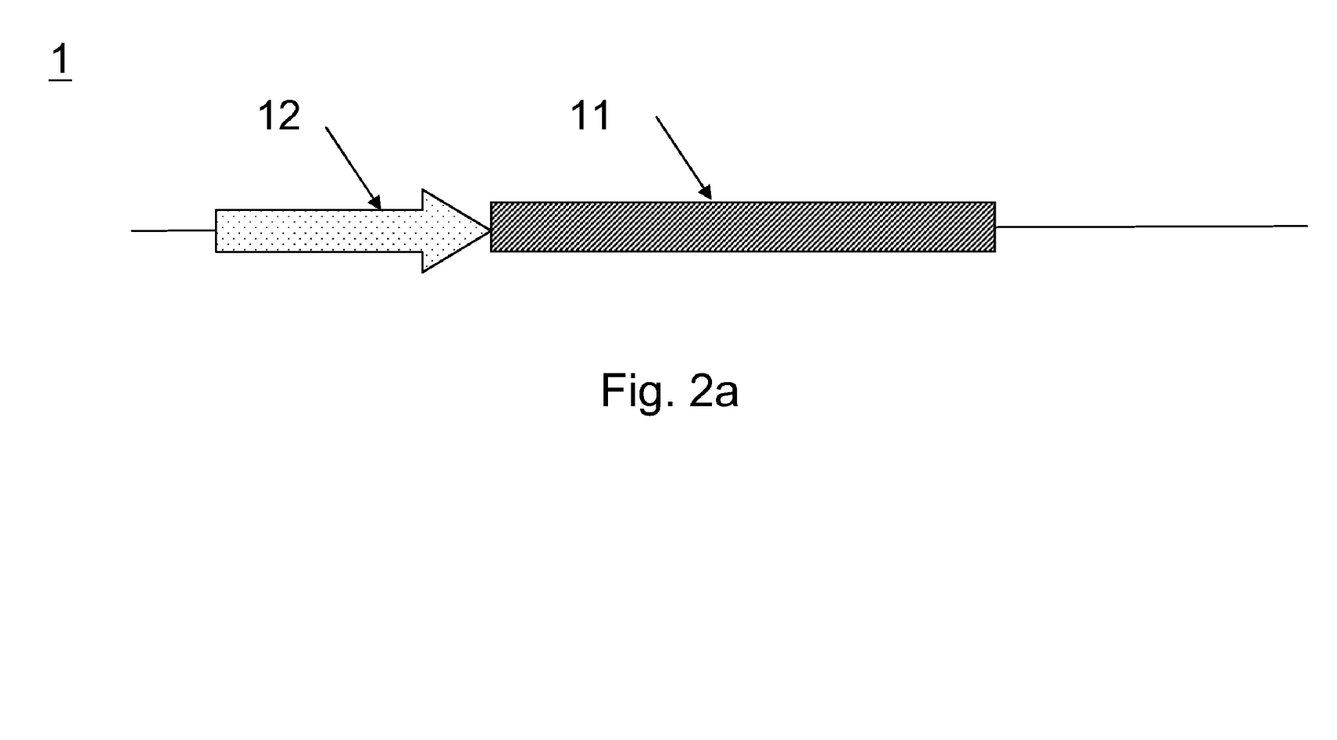
FIG. 2a to FIG. 2c is a diagram schematically illustrating recombinant baculovirus according to an embodiment of the present invention.
Figure 2B:
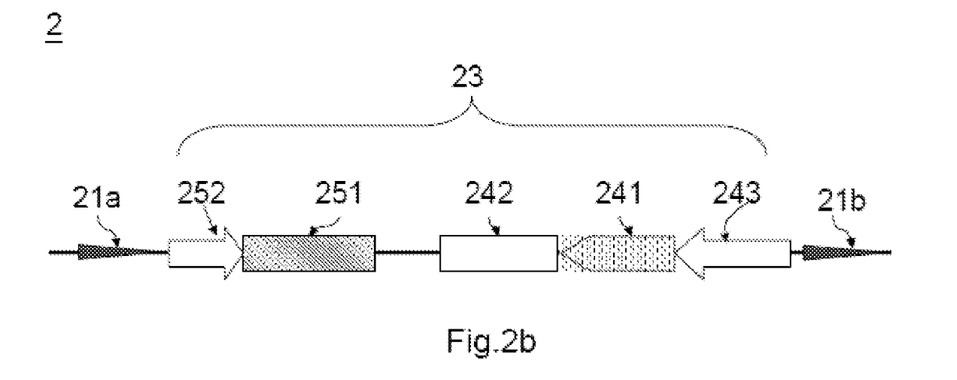

Referring to FIG. 1, FIG. 2a, and FIG. 2b; FIG. 1 is a flow chart schematically illustrating a preferred embodiment of the present invention; FIG. 2a and FIG. 2b are diagrams schematically illustrating a first recombinant baculovirus 1 and a second recombinant baculovirus 2 according to a preferred embodiment of the present invention.

At step S11, a first recombinant baculovirus 1 is provided, wherein the first recombinant baculovirus 1 includes a first expression cassette including a recombinase gene 11 and a first promoter 12 positioned upstream the recombinant gene 11.

At step S12, a second recombinant baculovirus 2 is provided, wherein the second recombinant baculovirus 2 includes a second expression cassette including two recombinase recognition sites 21 and an exogenous gene cassette 23 flanked by the recombinase recognition sites 21. The exogenous gene 23 includes a nuclear antigen gene 241, an origin of replication sequence 242, and a second promoter 243. A nuclear antigen is expressed by the nuclear antigen 241 and binds to the origin of replication sequence 242.

According to a preferred example of the present invention, the recombinase comprises a flipase recombination enzyme (FLP), wherein the corresponding recombinase recognition site is a flipase recognition target (Frt). For site-specific recombination, a site-specific recombinase, the FLP, recognizes the specific recombinase recognition sites and catalyzes highly efficient recombination between the Frt sequences. The FLP/Frt site-specific recombination occurs frequently, and the Frt sequence has not been discovered in certain model animals (e.g. $C.$ $elegans$, $Drosophila$, and mice) and human genome; therefore, FLP/Frt site-specific recombination is specific in mammalian cells.

According to another example, the recombinase comprises a cyclization recombination recombinase (CRE), wherein the corresponding recombinase recognition site is a locus of X-over P1 (loxp).

Furthermore, the episomal plasmid has to include an origin of replication sequence for the sustained replication and stable presence of transgenes in the cell. According to an example of the present invention, the origin of replication sequence 242 comprises a scaffold/matrix attachment region (S/MAR) element isolated from the interferon β-gene, that does not require any virally encoded trans-acting factors for episome replication. Therefore, an origin of replication sequence is sufficient for the sustained replication and stable presence of transgenes in the cell.

In another embodiment, the second recombinant baculovirus 2 further comprises a nuclear antigen gene, and a nuclear antigen is expressed by the nuclear antigen gene 241 and binds to the origin of replication sequence 242. For example, the origin of replication sequence 242 includes Epstein-Barr virus origin for stable episomal replication (EBV oriP), wherein the corresponding nuclear antigen is an EBV nuclear antigen 1 (EBNA-1). The oriP/EBNA-1 system includes the origin of replication sequence and the nuclear antigen adopted from the EB virus and drives one replication of the episomal plasmid when the cell replicates by the EBNA-1 interacts with OriP to distribute the episomal plasmids evenly to daughter cells for equivalent and stable presence of episomal plasmids in the cells during cell mitosis. According to another example of the present invention, the origin of replication sequence 242 comprises a Simian Virus 40 (SV40) origin of replication sequence, wherein the corresponding nuclear antigen is a SV40 large T antigen.

In a preferred embodiment of the present invention, the exogenous gene cassette 23 further includes a transgene 251 and a third promoter 252 positioned upstream the transgene 251.

The aforementioned promoters are used for enhancing gene expression, and therefore any one of the promoters presence is optional; any one of the promoters direction is the same as the gene to be enhanced; and the promoters may be constitutive or inducible. For example, the first promoter 12, the second promoter 243, and the third promoter 252 may include a cytomegalovirus immediate early (CMV-IE) promoter or a SV40 promoter.

Next, at step S13, the first recombinant baculovirus 1 and the second recombinant baculovirus 2 are used to co-transduce the mammalian cell, and the first expression cassette and the second expression cassette are introduced into the mammalian cell. A recombinase expressed by the recombinase gene 11 in the mammalian cell and recognizes and cuts the recombinase recognition sites 21a, 21b of the second gene cassette. The cut recombinase recognition sites 21a, 21b of the separated second gene cassette comprising the exogenous gene cassette are self-ligated, resulting in the formation of a circular episomal plasmid consisted of one recombinase recognition site and the exogenous gene cassette 23. The genome of the second baculovirus 2 may be rapidly decayed after the circular episomal plasmid formed, hence increasing the safety of the system. The circular episomal plasmid replicates itself for sustained expression of transgene 251 when the mammalian cell replicates.

Referring to FIG. 2b, the transgene 251 may comprise a reporter gene, e.g. an enhanced green fluorescence protein (EGFP), or a functional target gene.

The transgene 251 may comprise an antibiotics resistant gene, e.g. a neomycin resistant gene, used for increasing stability of the exogenous gene in the mammalian cell in the presence of an antibiotic. Therefore, an antibiotic may be added to provide a selective pressure for increasing stability of the exogenous gene cassette 23 of episomal plasmid in the mammalian cell.

Figure 2C:
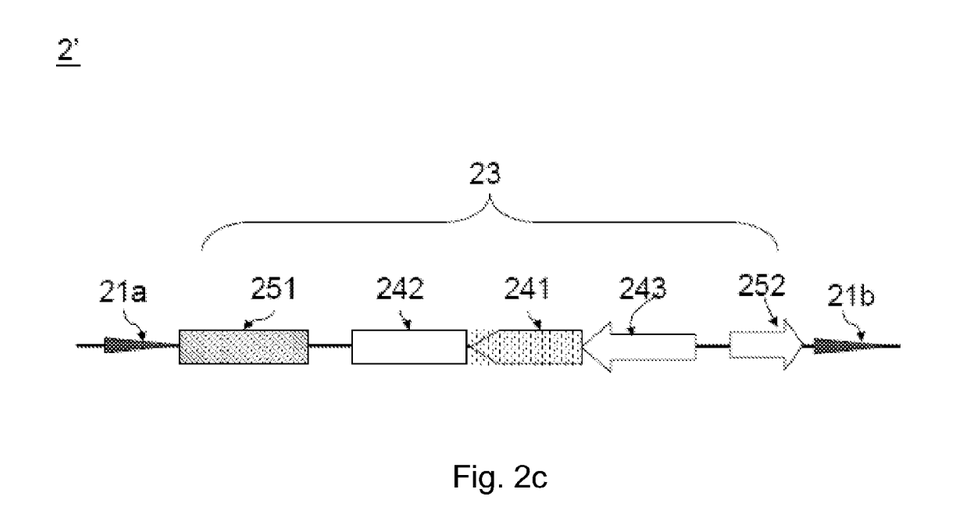

Referring to FIG. 2c, a second recombinant baculovirus 2' according to an example of the present invention is constructed for analyzing a percentage of the formation and expression of the circular episomal plasmid. The second recombinant baculovirus 2' is different from the second recombinant baculovirus 2 in the position of the third promoter 252, wherein the third promoter 252 of the second recombinant baculovirus 2' would be in the same direction with the transgene 251 as a result of site-specific recombination. In the present embodiment, the transgene 251 comprises a reporter gene, e.g. an egfp. Prior to the formation of the circular episomal plasmid, the third promoter 252 is not in the same direction as the egfp gene and hence unable to drive the expression of EGFP; after FLP-mediated circularization, the third promoter 252 is in the same direction with the egfp gene and drives the expression of EGFP. Therefore, a percentage of the fluorescent mammalian cell is detected to determine a percentage of the mammalian cell harboring the newly formed episome.

To sum up, the present invention provides a novel baculovirus as the genetic vector for safe and efficient gene delivery for gene therapy, which delivers the circular episomal plasmid by FLP-mediated recombination and prolongs the expression of exogenous gene by an origin of replication sequence.

The following descriptions of specific embodiments of the present invention have been presented for purposes of illustrations and description. They are not intended to be exclusive or to limit the invention to the precise forms disclosed, and obviously many modifications and variations are possible in light of the above teachings. It is intended that the scope of the invention be defined by the Claims appended hereto and their equivalents.

Figure 3:
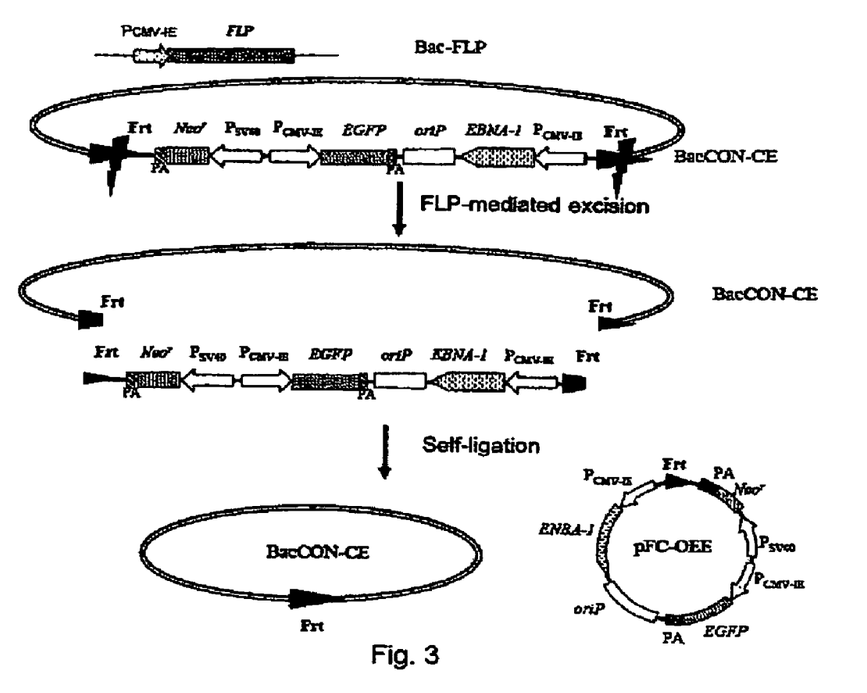
FIG. 3 is a diagram schematically illustrating an embodiment of the present invention.

FIG. 3 is a diagram schematically illustrating an embodiment of the present invention, wherein the first recombinant baculovirus (denoted as Bac-FLP) comprises an FLP gene (the recombinase gene 11) and a $P_{CMV-IE}$ (CMV-IE promoter, the first promoter 12); the second recombinant baculovirus (denoted as BacCON-CE) harbors the exogenous gene cassette 23 flanked by Frt (the recombinase recognition site 21). To facilitate the monitoring of initial transgene expression and genuine gene delivery efficiency of BacCON-CE, the vector that expresses the transgene 251 includes an egfp gene (the reporter gene) under the control of a $P_{CMV-IE}$ promoter and a Neo$^r$ (neomycin resistant gene, the antibiotics resistant gene) with a $P_{SV40}$ (SV40 promoter). The cassette also comprises EBNA-1 (the nuclear antigen gene 241), oriP (the origin of replication sequence 242), and $P_{CMV-IE}$ (the second promoter 243).

HEK293 cells are co-transduced with Bac-FLP (MOI 100) and BacCON-CE (MOI 400) and cultured in the presence or absence of 50 µg/ml G418. FLP is expressed by the FLP gene which is driven by the CMV-IE promoter ($P_{CMV-IE}$) in Bac-FLP and recognizes the Frt sites of BacCON-CE for site-specific recombination. After recombination, the exogenous gene cassette is thus cleaved off the BacCON-CE genome, and the Frt sequences are self-ligated to each other to form a circular episomal plasmid, pFC-OEE. The circular episomal plasmid is replicated once when the cell replicates, so that it is evenly distributed to daughter cells for stable presence and sustained expression of the exogenous gene cassette in the cells.

Figure 4A:
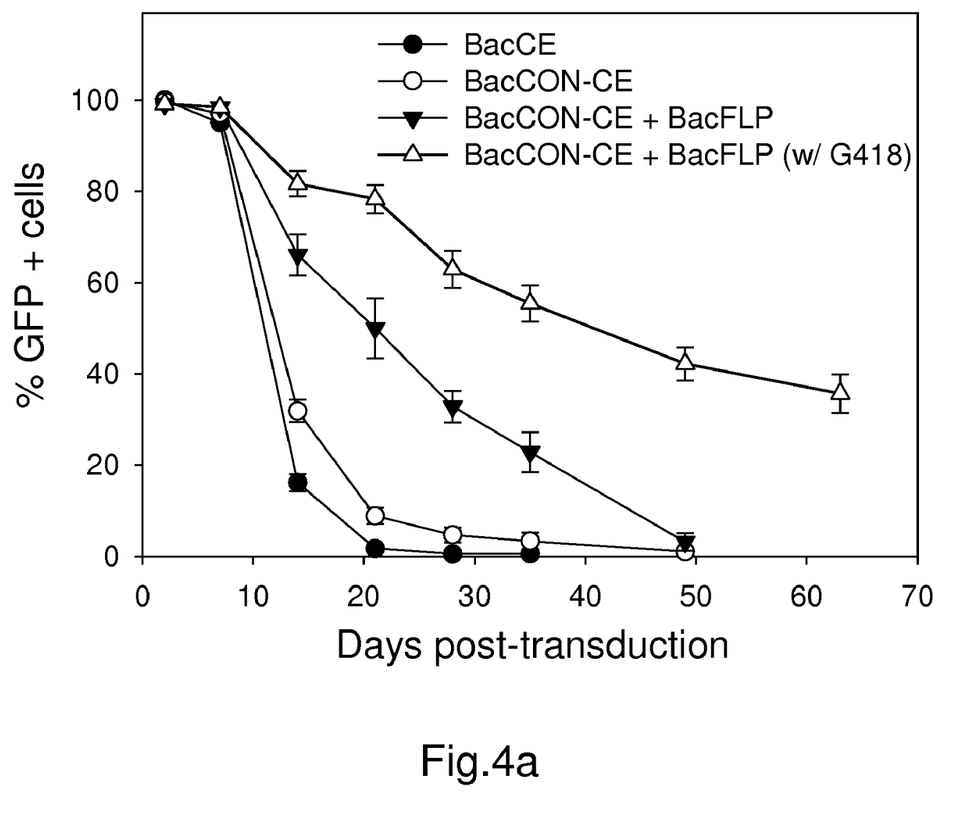
Figure 4B:
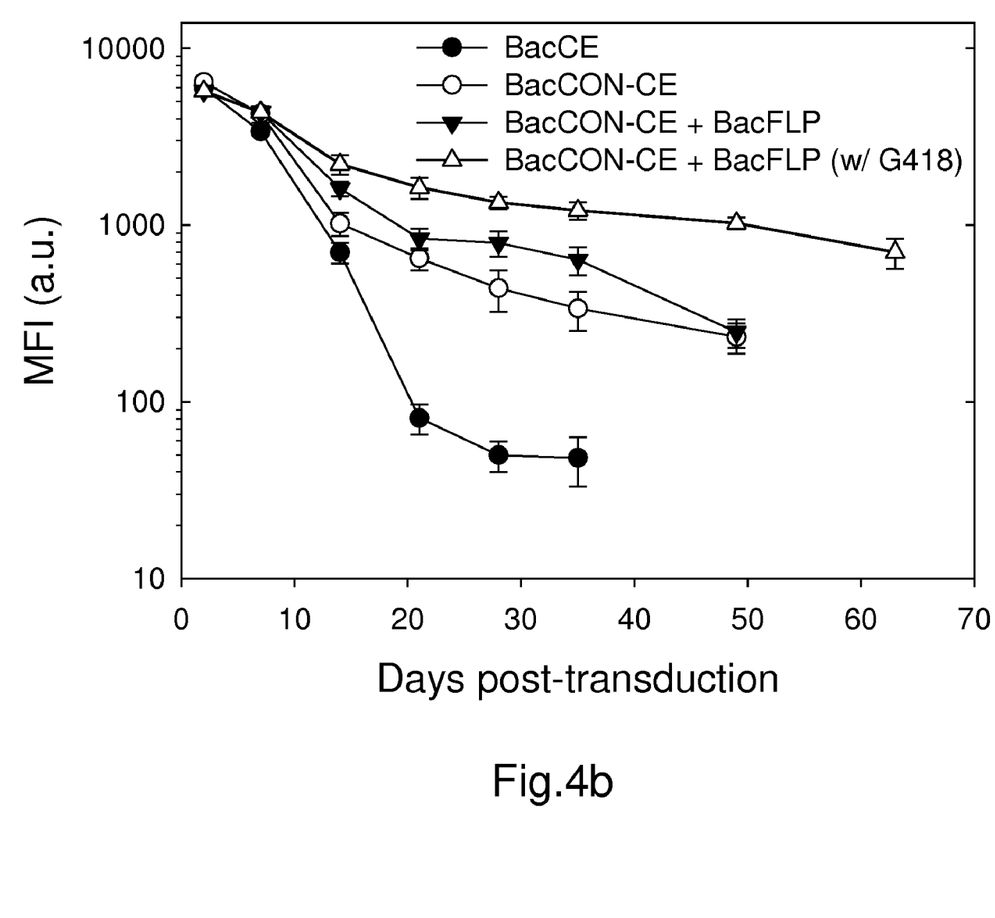

As shown in FIG. 4a and FIG. 4b, the cells are transduced with BacCON-CE (MOI 400) alone or with a typical baculovirus vector (Bac-CE) that transiently expresses egfp under the CMV-IE promoter (MOI 400). Under these transduction conditions, the % GFP+ cells approach 99-100% initially, but the GFP expression mediated by Bac-CE transduction underwent a rapid decay, with ≈16% and less than 5% cells emitting fluorescence at 14 and 20 dpt, respectively. By defining the time point at which the % GFP+ cells dropped below 5% as the expression duration, BacCON-CE transduction alone merely prolonged the expression to 28 days, but significantly elevated the mean fluorescence intensity (MFI). In the absence of G418, co-transduction with BacCON-CE and BacFLP considerably elevate the % GFP+ cells at 14 and 21 dpt to ≈66% and ≈50% with concurrent enhanced MFI. More importantly, the co-transduction extends the expression duration to at least 48 days. EGFP is expressed in the cells co-transduced with Bac-FLP and BacCON-CE for a prolonged period of time.

With the addition of G418, the insertion of Neo$^r$ gene in the cassette resulted in even more remarkable enhancement in gene expression level and duration, as 82%, 78%, 42% and 36% of transduced cells are EGFP-positive at 14, 21, 49 and 63 dpt, respectively, and the mean FI remained higher than 1000 throughout the culture period. Thus the duration of gene expression is extended to at least 63 days. Therefore, the present invention provides a method for sustained expression of an exogenous gene in cells.

Furthermore, a polymerase chain reaction (PCR) is performed to validate the generation of the episomal plasmid. A pair of primers are designed on the basis of Frt sequence (Frt-F: 5'-CGTGTACGGTGGGAGGTCTAT-3' and Frt-R:5'-GCCCT TGCTCACCATGGT-3') since the ligated Frt sequence is present in the plasmid pFC-OEE after recombination. As mentioned above, the exogenous gene cassette is separated from the baculovirus genome, and the Frt sequences are self-ligated to form a circular plasmid after FLP-catalyzed recombination; therefore, the PCR is thus performed to validate the formation and presence of the circular episomal plasmid.

Figure 5:
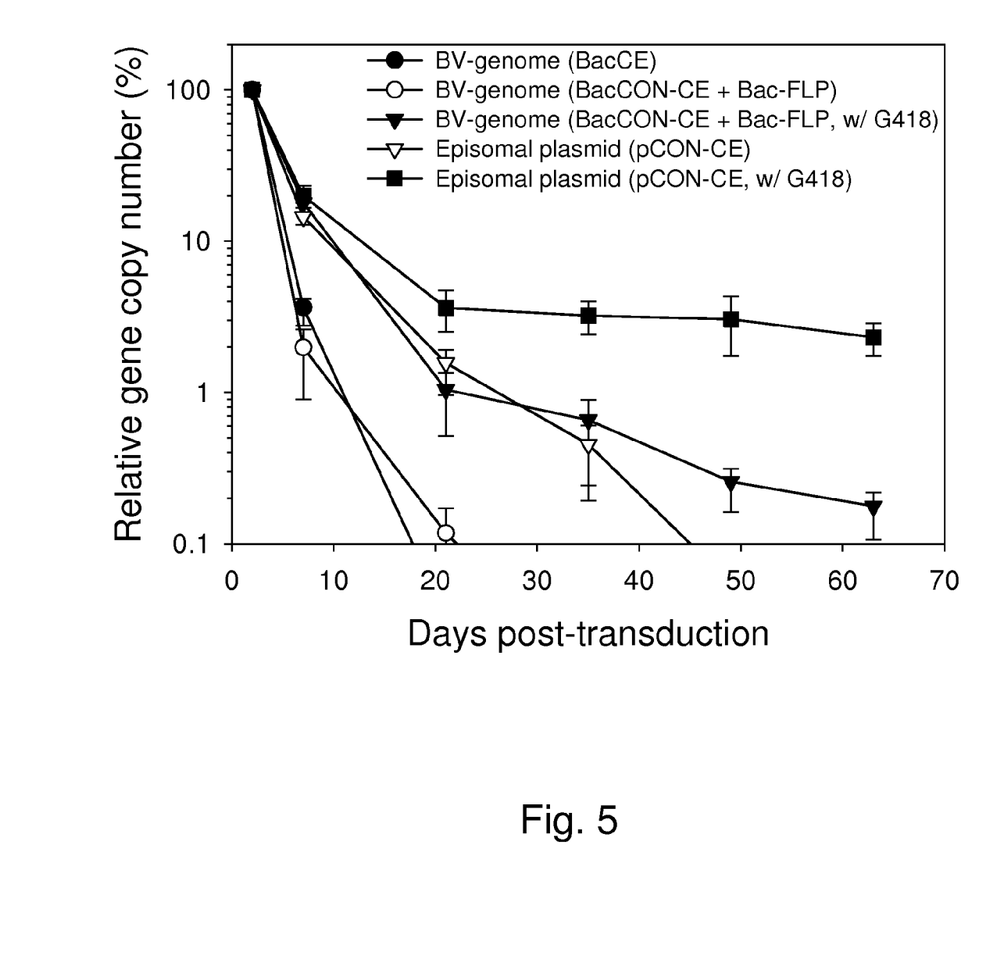

As mentioned above, the present invention provides a method for sustained expression of an exogenous gene in mammalian cells, which confers longer expression time than typical baculovirus vectors. A quantitative polymerase chain reaction (Q-PCR) is performed to validate whether the persistent fluorescence is an artifact of slow EGFP protein decay in the co-transduced cells or stemmed from the long-term maintenance of episomal plasmid pCON-CE. The primers are designed on the basis of Frt sequences: forward primer 5'-GGATCCATGATAAATTTAATTATTGATG-3' and reverse primer 5'-GGTACCTTATTTAGTATATTT-TAAGTG-3' since the ligated Frt sequence is present in plasmid pCON-CE after recombination. All data were normalized against those at 2 dpt to yield the relative copy number. FIG. 5a depicts that after single transduction with Bac-CE or co-transduction with BacCON-CE and BacFLP, baculoviral genome as probed by the primers targeting endogenous gp64 gene is rapidly degraded and virtually disappeared at 21 dpt. In contrast, the episomal plasmid pCON-CE as probed by the primers targeting the recombined Frt sites decayed at a slower rate even without the addition of G418, decreasing to 1.5% of the original episomal DNA at 21 dpt, and remained detectable until 45 dpt. By defining the time point at which the episomal DNA drops below 0.1% as the expression duration. Note that the data are obtained with internal control gene GAPDH, thus the decay of relative gene copy number arise from the dilution as well as degradation of genes in the cells. Strikingly, co-trasnduction with BacCON-CE and BacFLP, in conjunction with G418 addition, gave arise to stable maintenance of the episomal plasmid, which remain higher than 3.5% at 21 dpt and persist for at least 63 days. Under the same condition, the number of baculoviral genome still decay steadily with time albeit at a slow decay rate, and drop to 0.2% at 63 dpt. In conclusion, the sustained expression of the exogenous gene is caused by the stable presence of the episomal plasmid and may be further enhanced by adding an antibiotic to the incubating environment of the cells.

Figure 6A:
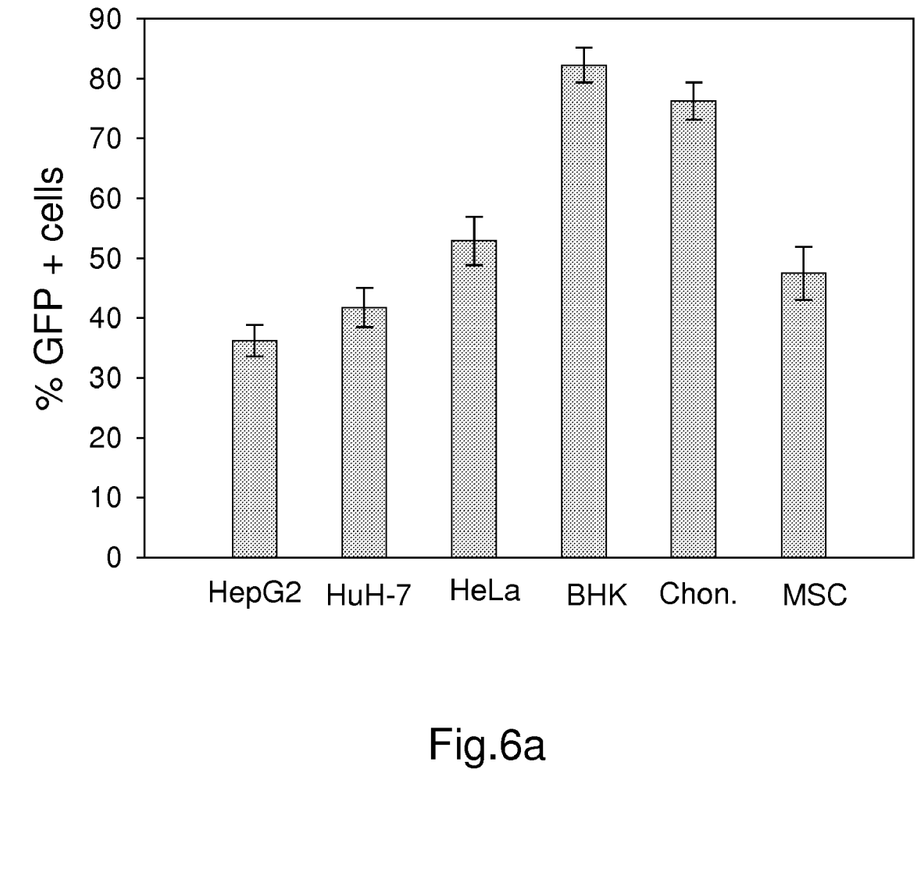
Figure 6B:
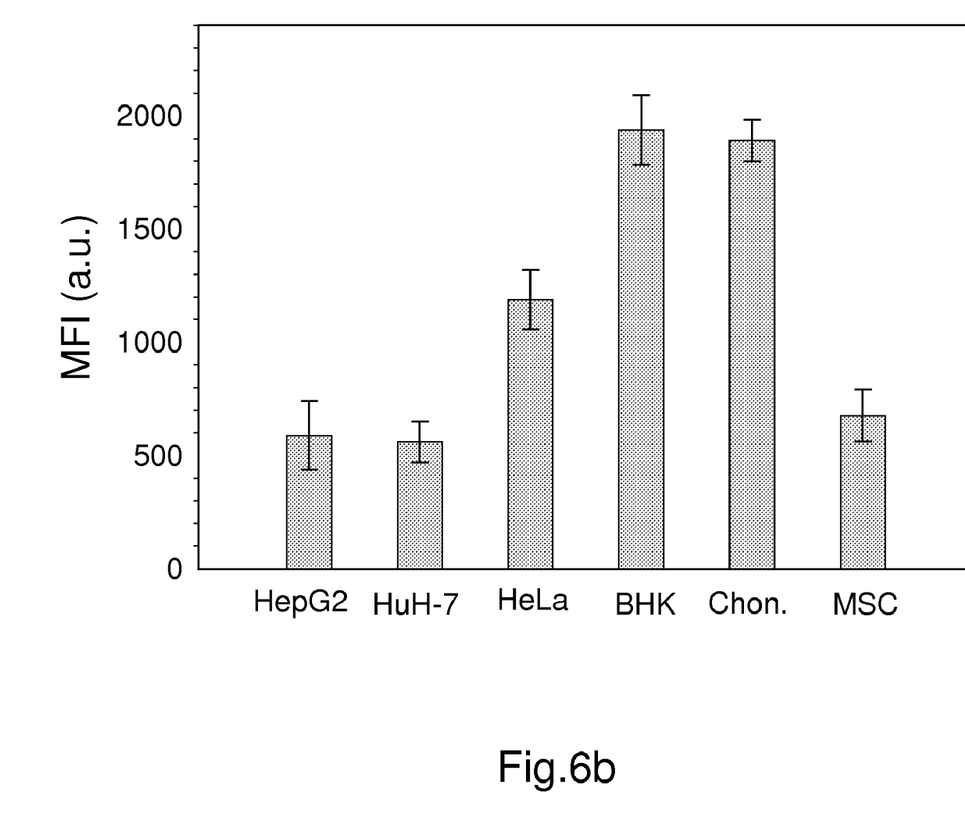

Conventional transfection method usually results in poor gene delivery into primary cell lines and mesenchymal stem cells. The present invention would test the efficiency of episomal plasmid delivery by transducing various kinds of cells and provide a novel delivery method in contrast to the conventional transfection method. Cells are transduced in accordance with the mentioned transduction procedure, and the percentage and fluorescence intensity of GFP+ cells carrying episomal plasmids formed by site-specific recombination are analyzed at second day post-transduction. As illustrated in FIG. 6a and FIG. 6b, the % GFP+ cells exceed 36% in all cell lines even for the difficult-to-transfect cell lines HepG2 and HuH-7. The % GFP+ cells (i.e. the recombination efficiency) are the highest in BHK cells (83%) and remain high in primary chondrocytes (77%) and MSCs (48%). These data indicate that our baculovirus system can deliver plasmids (which are formed intracellularly via FLP/Frt-mediated recombination) into more than 36% of HepG2 and Huh7 cells, 83% of BHK cells, 77% chondrocytes and 48% MSCs. Therefore this method represents a promising method to deliver plasmids into difficult-to-transfect cells and primary cells such as MSCs.

Since the FLP/Frt-based baculovirus system enables efficient plasmid formation within cells, the episome delivery efficiency via baculovirus-mediated transduction or lipid-mediated transfection are then compared. The cells are seeded ($\approx 5 \times 10^5$ cells/well) and cultured overnight followed by co-transduction with BacFLP (MOI 100) and BacFC-OEE (MOI 400), or transfection with a control plasmid ($\approx 6.5 \times 10^{11}$ copies/well) by lipofectamine™ 2000. With this design, $\approx 800$-$1100$ times more egfp gene is introduced by transfection ($\approx 6.5 \times 10^{11}$ copies) than by transduction ($\approx 6.0$-$8.0 \times 10^8$ copies from $2.0 \times 10^8$ pfu per well, by assuming that 1 pfu is equivalent to 3-4 baculovirus particles) wherein the resultant % GFP+ cells are significantly higher in the transduced (42%, 48% and 76% for HuH-7, MSC and chondrocytes, respectively) than in the transfected cells (9%, 3% and 7% for HuH-7, MSC and chondrocytes, respectively) (not shown), demonstrating the significantly more efficient transgene expression mediated by baculovirus-carried gene cassettes.

The plasmid delivery method of the present invention may be applicable in gene therapy and tissue engineering to solve the low transfection rate of transgene, prolong the transgene expression and circumvent the safety concerns regarding gene integration.

To sum up, a method of sustained expression of an exogenous gene according to the present invention effectively transduces various kinds of cells and improves the expression time of baculovirus to more than 60 days. The present invention has following advantages in gene delivery.

1. Efficiency: baculovirus is an efficient gene delivery vector; therefore high transduction efficiency and generation efficiency of episomal plasmid is achieved by adopting baculovirus to transduce mammalian cells.
2. Cost-saving: conventional transfection agents used in plasmid transfection, e.g. a liposome (which is expensive), is not a necessity for the present invention.
3. Time-saving: baculovirus is easily scaled up to obtain high-titer virus with advantages of saving operation time and cost.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A method for sustained expression of an exogenous gene, comprising:
   providing a first recombinant baculovirus comprising a first expression cassette including a recombinase gene;
   providing a second recombinant baculovirus comprising a second expression cassette, wherein the second expression cassette includes two recombinase recognition sites and an exogenous gene cassette flanked by the recombinase recognition sites, wherein the exogenous gene cassette comprises an origin of replication sequence; and
   co-transducing the first recombinant baculovirus and the second recombinant baculovirus to a mammalian cell, whereby the first expression cassette and the second expression cassette are introduced into the mammalian cell, wherein
   a recombinase expressed by the recombinase gene recognizes and cuts the recombinase recognition sites of the second expression cassette;
   the second expression cassette is cleaved off from the genome of the second recombinant baculovirus; and
   the cut recombinase recognition sites of the separated second expression cassette comprising the exogenous gene cassette are self-ligated to form a circular episomal plasmid consisting of one recombinase recognition site and the exogenous gene cassette for sustained expression of the exogenous gene cassette.

2. The method as claimed in claim 1, wherein the first recombinant baculovirus further comprises a first promoter positioned upstream the recombinase gene.

3. The method as claimed in claim 1, wherein the origin of replication sequence is a scaffold matrix attachment region (S/MAR) element.

4. The method as claimed in claim 1, wherein the second recombinant baculovirus further comprises a nuclear antigen gene, and a nuclear antigen is expressed by the nuclear antigen gene and binds to the origin of replication sequence.

5. The method as claimed in claim 4, wherein the origin of replication sequence comprises an Epstein-Barr virus origin for plasmid replication (EBV oriP).

6. The method as claimed in claim 5, wherein the nuclear antigen gene comprises an EBV nuclear antigen 1 (EBNA-1).

7. The method as claimed in claim 4, wherein the origin of replication sequence comprises a Simian Virus 40 (SV40) origin of replication sequence.

8. The method as claimed in claim 7, wherein the nuclear antigen gene comprises a SV40 large T antigen.

9. The method as claimed in claim 4, wherein the exogenous gene cassette further comprises a second promoter positioned upstream to the nuclear antigen gene and being in the same direction as the nuclear antigen gene in the circular episomal plasmid.

10. The method as claimed in claim 1, wherein the exogenous gene cassette further comprises a transgene.

11. The method as claimed in claim 10, wherein the transgene comprises a reporter gene or a functional target gene.

12. The method as claimed in claim 11, wherein the reporter gene comprises an enhanced green fluorescence protein (EGFP).

13. The method as claimed in claim 12, further comprising a step of detecting a percentage of the fluorescent mammalian cell to determine a percentage of the mammalian cell comprising the exogenous gene cassette.

14. The method as claimed in claim 10, wherein the transgene comprises an antibiotics resistant gene.

15. The method as claimed in claim 14, further comprising a step of adding an antibiotic to provide a selective pressure for enhancing stability of the exogenous gene cassette.

16. The method as claimed in claim 10, wherein the exogenous gene cassette further comprises a third promoter positioned upstream to the transgene and being in the same orientation as the transgene.

17. The method as claimed in claim 1, wherein the recombinase comprises a flipase recombination enzyme (FLP).

18. The method as claimed in claim 17, wherein the recombinase recognition sites comprise flipase recognition target (Frt).

19. The method as claimed in claim 1, wherein the recombinase comprises a cyclization recombination recombinase (CRE).

20. The method as claimed in claim 19, wherein the recombinase recognition sites comprise a locus of X-over P1 (loxP).

21. The method as claimed in claim 1, wherein the genome of the second baculovirus is rapidly decayed after the circular episomal plasmid is formed.

22. The method as claimed in claim 1, wherein, the circular episomal plasmid replicates itself when the mammalian cell replicates.

* * * * *